(12) United States Patent
Mastrodonato et al.

(10) Patent No.: US 7,262,180 B2
(45) Date of Patent: Aug. 28, 2007

(54) COMPOSITIONS AND METHODS FOR THE TREATMENT OF INFLAMMATORY CONDITIONS OF MUCOSAE, SKIN AND THE EYE

(75) Inventors: Marco Mastrodonato, Milan (IT); Roberto Ciattini, Milan (IT)

(73) Assignee: Sinclair Pharmaceuticals, Ltd., Surrey (GB)

( * ) Notice: Subject to any disclaimer, the term of this patent is extended or adjusted under 35 U.S.C. 154(b) by 332 days.

(21) Appl. No.: 10/963,848

(22) Filed: Oct. 12, 2004

(65) Prior Publication Data

US 2005/0143324 A1 Jun. 30, 2005

Related U.S. Application Data

(63) Continuation-in-part of application No. PCT/EP03/03329, filed on Mar. 31, 2003.

(30) Foreign Application Priority Data

Apr. 9, 2002 (IT) .......................... MI2002A0756

(51) Int. Cl.
 A61K 31/728 (2006.01)
 A61K 31/427 (2006.01)
 A61K 31/19 (2006.01)
 A61K 31/60 (2006.01)

(52) U.S. Cl. .................. 514/54; 514/365; 514/569; 514/568

(58) Field of Classification Search ................. 514/365
See application file for complete search history.

(56) References Cited

U.S. PATENT DOCUMENTS

| | | | |
|---|---|---|---|
| 4,874,774 A | | 10/1989 | Ushimaru et al. |
| 4,963,527 A | | 10/1990 | Bombardelli et al. |
| 5,422,118 A | * | 6/1995 | Brown et al. ............... 424/449 |
| 5,470,874 A | | 11/1995 | Lerner |
| 5,945,409 A | * | 8/1999 | Crandall ..................... 514/78 |

FOREIGN PATENT DOCUMENTS

| | | |
|---|---|---|
| EP | 0694305 | 1/1996 |
| IT | 1215469 | 2/1990 |
| JP | 6336421 | 12/1994 |

OTHER PUBLICATIONS

Gianotti, A. "Telemestein and variations in blood concentrations of lipoprotein A" La Clinica terapeutica (1994) vol. 145, No. 10, pp. 283-385.*

Vinson et al., "Beneficial effects of a novel IH636 grape seed proanthocyanidin extract and a niacin-bound chromium in a hamster atherosclerosis model" Molecular and Cellular Biochemistry (2002) vol. 240, pp. 99-103.*
Zakirov et al., "The hypolipidemic and antiatherosclerotic properties of the ammonium salt of glycyrrhetic acid and of 18-dehydroglycyrrhetic acid" Eksperimental'naia i klinicheskaia farmakologiia (1996) vol. 59, No. 5, pp. 53-55.*
Nicolosi et al. "Vitamin E Reduces Plasma Low Density Lipoprotein Cholesterol, LDL Oxidation, and Early Aortic Atherosclerosis Compared with Black Tea in Hypercholesterolemic Hamsters" Nutrition Research (1999) vol. 19, No. 8, pp. 1201-1214.*
Kadir et al., "Alpha-Bisabolol, a possible safe penetration enhancer for dermal and transdermal therapeutics" International Journal of Pharmaceutics (1991) vol. 70, pp. 87-94.*
Remington: The Science and Practice of Pharmacy, 20th Edition, (2000) Published by the Philadelphia College of Pharmacy and Science, Edited by Alfonso R. Gennaro et al., pp. 836-844 and 917-918.*
Ashcroft et al., J. of Clin. Pharm. and Therap., 25:1-10 (2000).
Greaves, New England J. of Medicine, 332:581-588 (1995).
Langer, Science, 249:1527-1533 (1990).
Nevitt et al., British J. of Dermatology, 135:533-537 (1996).
Roenigk et al., J. of the Am. Acad. of Dermatology, 1:145-156 (1988).
Stern, Cancer, 73:2759-2764 (1994).
Stern, Dermatol. Clin., 13:717-722 (1995).
Treat et al., Liposomes in the Therapy of Infectious Disease and Cancer, Lopez-Berestein and Fidler (eds.) Liss, New York, 353-365 (1989).

* cited by examiner

Primary Examiner—Shaojia Anna Jiang
Assistant Examiner—Eric Olson
(74) Attorney, Agent, or Firm—Marshall, Gerstein & Borun LLP

(57) ABSTRACT

The present invention relates to compositions comprising telmesteine, glycyrrhetinic acid, and a proanthocyanidin, as well as methods for using such compositions in the treatment of an inflammatory condition of the skin including, but not limited to, atopic dermatitis(eczema), allergic contact dermatitis, seborrheic dermatitis, psoriasis, *xerosis* and atopia, as well as treatment of an inflammatory condition of mucosae and of an inflammatory condition in the eye. The present invention also relates to compositions comprising a proanthocyanidin, glycyrrhetinic acid and telmesteine, as well as methods for using such compositions in the treatment of an inflammatory condition of the skin including, but not limited to, atopic dermatitis, allergic contact dermatitis, seborrheic dermatitis, radiation dermatitis, psoriasis, *xerosis* and atopia, as well as treatment of an inflammatory condition of mucosae and of an inflammatory condition in the eye.

22 Claims, No Drawings

COMPOSITIONS AND METHODS FOR THE TREATMENT OF INFLAMMATORY CONDITIONS OF MUCOSAE, SKIN AND THE EYE

The present application is a continuation-in-part of International Patent Application No. PCT/EP03/03329 filed Mar. 31, 2003 designating the United States, which was published in English as International Patent Publication No. WO 03/084553 on Oct. 16, 2003, which in turn claims priority benefits of Italian Patent Application No. MI 2002 A 000756, filed Apr. 9, 2002, the disclosures of each of which are incorporated herein by reference in their entirety.

1. FIELD OF THE INVENTION

The present invention relates to compositions comprising a proanthocyanidin, as well as methods for using such compositions in the treatment of an inflammatory condition of the skin including, but not limited to, atopic dermatitis (eczema), allergic contact dermatitis, seborrheic dermatitis, radiation dermatitis, psoriasis, *xerosis* and atopia, as well as treatment of an inflammatory condition of mucosae and of an inflammatory condition in the eye. The present invention also relates to compositions comprising a proanthocyanidin, glycyrrhetinic acid and telmesteine, as well as methods for using such compositions in the treatment of an inflammatory condition of the skin including, but not limited to, atopic dermatitis, allergic contact dermatitis, seborrheic dermatitis, radiation dermatitis, psoriasis, *xerosis* and atopia, as well as treatment of an inflammatory condition of mucosae and of an inflammatory condition in the eye.

2. BACKGROUND OF THE INVENTION

Dermatitis is a superficial inflammation of the skin, characterized by vesicle formation, erythema, edema, oozing, scaling or crusting lesions, and intense itching. Different types of dermatitis can be distinguished: contact dermatitis, caused by irritants in contact with the skin or by non-irritating substances, to which the subject is allergic; atopic dermatitis, characterized by strong itching and chronic course; seborrheic dermatitis, a scaling disease mainly affecting the face and scalp. In principle, the treatment consists in removing the etiological agent; however, frequently such agent cannot be identified or removed.

One particular form of dermatitis is psoriasis, which is a chronic, inflammatory, hyperproliferative skin disease that affects approximately 1-2% of the general population with men and women affected in equal numbers (Nevitt, G. J. et al., 1996, British J. of Dermatology 135:533-537). Approximately 150,000 new cases of psoriasis and approximately 400 deaths from psoriasis are reported each year (Stern, R. S., 1995, Dermatol. Clin. 13:717-722). The impact of psoriasis on the lives of patients goes beyond the effects on their physical appearance; it can also negatively impact their physical capacity and longevity. The most common type of psoriasis is chronic plaque syndrome. The condition is chronic for many sufferers and consists of periods of remission and relapse during the course of the disease (Ashcroft, D. M., et al., 2000, J. of Clin. Pharm. And Therap. 25:1-10). Psoriasis is characterized by indurated, erythematous scaling plaques most commonly located on the scalp or the extensor aspects of the elbows and knees, but may occur at any skin site.

Traditionally, treatment of such dermatitis has been based on corticosteroids, which involves well known side effects such as reduced immune defense resulting in a secondary bacterial infection, particularly of fungi or *Candida*. Further, such treatment requires frequent suspension of the treatment, and such treatment cannot be used during the exudative acute phase of the dermatitis. Furthermore, prolonged use of corticosteroids should be avoided, especially in pregnant women and in children, as systemic side effects can occur.

The present treatment options currently available for psoriasis include topical agents, phototherapy and systemic agents. Topical treatments are first-line therapy for patients with mild to moderate plaque psoriasis. Systemic treatment is generally prescribed for severe cases of psoriasis where topical therapy is either impractical or ineffective. Phototherapy can be administered either alone or in combination with either topical or systemic agents. In selecting a suitable treatment, consideration should be given to the overall severity of the disease, the body areas involved, that patient's age, sex, general health, previous treatment and preferences.

Topical agents available for the treatment of psoriasis include emollients, keratolytics, coal tar, topical corticosteroids, dithranol (anthralin), topical vitamin D3 analogues and tazarotene. Unfortunately, these topical agents are associated with side effects such as irritation, toxicity and possible carcinogenicity (Ashcroft, D. M., et al., 2000, J. of Clin. Pharm. and Therap. 25:1-10).

Examples of phototherapy for psoriasis include ultraviolet B radiation (UVB) phototherapy and ultraviolet A photochemotherapy (PUVA). UVB phototherapy employs broadband (290-320 nm) sources and is useful in the management of moderate to severe psoriasis and is generally administered to patients whose disease is refractory to topical therapy. Treatment is usually administered two to three times a week with coal tar often being applied prior to exposure. UVB phototherapy must be carefully regulated, however, due to the short-term risks of erythema and vesiculation and the long-term risks or premature skin aging. PUVA therapy combines long wave (320-400 nm) ultraviolet A irradiation with oral or topical administration of psoralens. The two psoralens traditionally used, 5- and 8-methoxypsoralen (MOP) are believed to intercalate into DNA and inhibit cell proliferation upon activation by UVA radiation. PUVA therapy is generally administered twice weekly. Unfortunately, PUVA commonly causes short-term risks such as nausea, erythema, headache and skin pain as well as long-term risks of actinic keratoses, premature ageing of the skin, irregular pigmentation and squamous cell carcinoma which is reported in a quarter of patients (Stern, R. S., 1994, Cancer 73:2759-2764).

Systemic agents currently used to treat psoriasis include methotrexate (MTX), cyclosporin, acitretin and hydroxyurea. There are adverse side effects associated with each of these agents, however, and most are unavailable to pregnant patients. In particular, methotrexate, which is considered to be the 'gold standard' for treatment of severe psoriasis, carries a risk of hepatotoxicity with long-term use. In addition, it is recommended that patients have a liner biopsy performed at or near the start of each treatment and after each cumulative dose of 1.0-1.5 mg MTX (Roenigk, H. H. et al., 1988, J. of the Am. Acad. of Dermatology).

When patients are provided with information regarding the possible adverse effects of the currently available therapies for psoriasis, many often choose to live with the condition rather than undergo treatment (Greaves M. W., 1995, New England J. of Medicine 332:581-588). Other alternative treatments known in the art for dermatitis are based on hydrogenated vegetable oils, hydrophilic petrolatum, or medicated shampoos (based on zinc-pyrithione, selenium sulfide, sulfur and the like) in the case of seborrheic dermatitis, and are often unsuccessful.

In the case of the mucosal inflammatory conditions, in particular of mouth, gingival, rectal, vaginal and eye mucosae, a number of topical treatments are available, including the use of steroidal or non-steroidal anti-inflammatory agents, with the problems and side effects characteristics for these medicaments.

Different uses of proanthocyanidins have been described in the pharmaceutical and cosmetic fields. EP 0 694 305 discloses topical compositions of proanthocyanidins combined with coumarins (esculoside and the like) for the treatment of peripheral vasculopathies, such as bedsores, scars, couperose, varices and the like. U.S. Pat. No. 5,470, 874 describes a combination of proanthocyanidins and vitamin C for the topical use, as sunscreen, for stimulating collagen synthesis and for restoring damaged collagen. Finally, JP 6,336,421 relates to topical formulations of proanthocyanidins combined with anti-inflammatories, among which glycyrrhetinic acid and derivatives are cited, for cosmetic use and against sunburns. However, to date the use of proanthocyanidins in the treatment of pathologies such as chronic dermatitis, seborrheic dermatitis and allergic dermatis has not been described.

Proanthocyanidins are widely diffused in a number of vegetable species. They are vegetable extracts containing bioflavonoids, with well-defined chemical profile, consisting for about 15% of dimers, about 20% of trimers and tetramers, and of small amounts of catechin and epicatechin. They also contain essential fatty acids similar to those of the skin hydrolipidic barrier, which contribute to keep said barrier intact. Finally, proanthocyanidins reduce the concentration of enzymes such as elastase, collagenase, hyaluronidase and beta-glucuronidase, which are responsible for the destruction of elastin, collagen and hyaluronic acid proteins. Therefore, proanthocyanidins are widely used in the pharmaceutical and cosmetic industries, thanks to their restoring, regenerating, nutrient and restructurant actions, which restores the skin elasticity and tonicity.

18-β-Glycyrrhetinic acid, extracted from the roots of *Glycyrrhiza glabra*, is known to have anti-inflammatory properties on the skin, in particular in burns and redness.

Telmesteine (N-carbethoxy-4-thiazolidinecarboxylic acid), described in Italian Patent No. 1,215,469, exerts antiradicalic and protective action against the oxidizing agents responsible for skin damages. Methods for making Telmesteine are described, for example, in U.S. Pat. No. 4,874,774 to Quadro, the disclosure of which is incorporated by reference herein in its entirety. Telmesteine, and alkali and alkali-earth of basic amino acid salts thereof, have anti-mucolytic activity and inhibit elastase and collagenase, and are known to be useful in the treatment of respiratory tract disorders such as emphysema and fibrosis.

There remains a great need in the art for therapies with improved activity than currently available drugs and treatment regiments for the prevention, treatment or amelioration of dermatological diseases and disorders such as dermatitis and psoriasis.

Citation or identification of any reference in Section 2 or in any other section of this application shall not be construed as an admission that such reference is available as prior art to the present invention.

3. SUMMARY OF THE INVENTION

The present invention is directed to a composition suitable for topical administration, which composition comprises a proanthocyanidin, glycyrrhetinic acid and telmesteine, or pharmaceutically acceptable salts thereof, as the active ingredient, and a pharmaceutically acceptable carrier or excipient. In certain embodiments, the composition is suitable for topical administration and is in the form of a cream, gel, lotion, suspension, spray or ointment. In a preferred embodiment, the proanthocyanidin is in a complex with phospholipids.

The present invention is also directed to a method of treating or preventing an inflammatory condition of the mucosae, skin or the eye comprising topically administering to the site of the condition a composition comprising a proanthocyanidin, glycyrrhetinic acid and telmesteine, or pharmaceutically acceptable salts thereof, as the active ingredient, and a pharmaceutically acceptable carrier or excipient in an amount effective to treat or prevent such condition. In another embodiment, the present invention is directed to a method of treating or preventing atopic dermatitis, allergic contact dermatitis, seborrheic dermatitis, *xerosis*; psoriasis or atopia comprising topically administering a composition comprising proanthocyanidins, or a pharmaceutically acceptable salt thereof, as the active ingredient, and a pharmaceutically acceptable carrier or excipient to a subject in need of such treatment or prevention in an amount effective to treat or prevent atopic dermatitis, allergic contact dermatitis, seborrheic dermatitis, *xerosis*, psoriasis or atopia.

The present invention is also directed to a method of ameliorating at least one symptom of an inflammatory condition comprising topically administering to the site of the condition a composition comprising a proanthocyanidin, glycyrrhetinic acid and telmesteine, or pharmaceutically acceptable salts thereof, as the active ingredient, and a pharmaceutically acceptable carrier or excipient in an amount effective to ameliorate at least one symptom associated with such condition.

More particularly, the compositions of the present invention are also useful as moisturizers and lenitives for sensitive, delicate skins or to treat or ameliorate allergic irritations caused by medicaments, detergents, solvents; treat, prevent or ameliorate erythema subsequent to excessive exposure to sun radiation. In other embodiments of the present invention, the compositions are useful in treating or ameliorating effects caused by insect bites, redness of various origin, post-shaving irritations, slight burns, cutaneous hyper-reactivity, as well as a normalizer after treatments of aesthetic medicine, such as skin peeling with glycolic acid or laser therapy. Additional exemplary inflammatory conditions that can be treated or prevented in accordance with the present invention are listed infra.

As used herein, the terms "subject" and "patient" are used interchangeably. As used herein, the terms "subject" and "subjects" refer to an animal, preferably a mammal including a non-primate (e.g., a cow, pig, horse, cat, dog, rat, and mouse) and a non-primate (e.g., a monkey such as a cynomolgous monkey and a human), and more preferably a human.

As used herein, the terms "prevent", "preventing" and prevention refer to the prevention of the recurrence or onset of one or more symptoms of a inflammatory condition of the mucosae, skin or the eye in a subject resulting from the administration of a prophylactic or therapeutic agent, i.e., a composition comprising proanthocyanidins in a complex with phospholipids. As used herein, the term "prophylactically effective amount" refers to that amount of the prophylactic agent sufficient to result in the prevention of the recurrence or onset of one or more symptoms of a condition.

As used herein, the terms "treat", "treatment" and "treating" refer to the amelioration of one or more symptoms associated with an inflammatory condition of the mucosae, skin or the eye that results from the administration of a composition of the present invention. In certain embodiments, such amelioration includes, e.g., a reduction in the erythema, edema, oozing, scaling or crusting lesions and/or intense itching of the skin. In other embodiments, amelioration also includes the elimination of, or a reduction in the amount of, one or more traditional medications used in treating the disease or disorder, such as corticosteroids. Thus, in certain embodiments where a composition of the invention is topically administered separately with one or more traditional medications, the amount of the traditional medication necessary is reduced due to co-administration with a composition of the invention.

The present invention can be more fully explained by reference to the following detailed description and illustrative examples.

4. DETAILED DESCRIPTION OF THE INVENTION

The present invention is directed to a composition suitable for topical administration, which composition comprises a proanthocyanidin, glycyrrhetinic acid and telmesteine, or pharmaceutically acceptable salts thereof, as the active ingredient, and a pharmaceutically acceptable carrier or excipient. In certain embodiments, the composition is suitable for topical administration and is in the form of a cream, gel, lotion, suspension, spray or ointment. In a preferred embodiment, the proanthocyanidin is in a complex with phospholipids. In certain embodiments, the composition is in the form of a cream, gel, lotion, suspension, spray or ointment.

The compositions of the invention can be used by themselves or in admixture with one or more medicaments, excipients and/or adjuvants, preferably forming a viscous and lubricating substance that remains adherent to the surface epithelium. These compositions are suitable for topical administration to epithelial surfaces such as the skin.

Optionally, the compositions of the present invention may further contain one or more other ingredients, such as an antibacterial, disinfectant, antifungal, analgesic, emollients, local anaesthetics and the like. Suitable antimicrobials include, but are not limited to, quaternary ammonium salts such as benzalkonium chloride.

In preferred embodiments of the invention, the proanthocyanidins are extracted from grape seeds and skin of *Vitis vinifera*. Most preferred are the complexes of proanthocyanidins from *Vitis vinifera* with phospholipids, prepared according to the process disclosed in U.S. Pat. No. 4,963, 527, the contents of which are hereby incorporated by reference in its entirety herein.

The topical pharmaceutical compositions of the present invention will contain the active ingredients in admixture with a suitable carrier, preferably a carrier rich in polyunsaturated fatty acids. According to the invention, suitable carriers comprise squalene, fatty acids, fatty acids esters, vegetable oils, natural or synthetic triglycerides. More preferably, suitable carriers comprise squalene, karite butter, octyl palmitate and oenothera oil. In particular, karite butter (also known as shea butter) is a fat consisting of a mixture of saturated and unsaturated fats, extracted from the seeds of *Butirospennum parkii*, a tree from northern Africa, which is used in cosmetics thanks to its protective and softening actions, which make it particularly useful for sensitive skins as well as for skins which easily redden.

*Oenothera* oil (also known as evening primrose oil), extracted from the plant *Oenothera biennis*, is rich in essential polyunsaturated fatty acids, in particular y-linolenic acid, indispensable for regenerating the skin and all cellular tissues.

According to a preferred embodiment, the pharmaceutical compositions of the invention will further contain compounds with antioxidizing activity, such as tocopherols and ascorbic acid or esters thereof, preferably tocopherol acetate and ascorbyl palmitate or tetrapalmitate, to further increase the protective effect on cell membranes and to slow down the oxidation of polyunsaturated fatty acids.

The compositions of the present invention may further contain other active ingredients, with complementary or anyway useful actions in the treatment of inflammatory conditions of the mucosae, skin or the eye, e.g., dermatosis.

Examples of said active ingredients are:
salicylic acid, which exerts a keratolytic action useful for the treatment of seborrheic dermatitis;
hyaluronic acid, which is useful for the treatment of radiation dermatitis due to its hydrating and healing action;
alpha-bisabolol, one of the active principles present in chamomile essential oil (*Matricaria flos*), which has lenitive and anti-redness action;
zinc picolate, which exerts slightly astringent, emollient and lenitive actions, blocks and prevents the formation of free radicals thanks to its competitive action towards iron ions, and is active in the enzymatic processes of skin metabolism;
allantoin which has astringent, slightly keratolytic and healing actions; moisturizers or wetting agents;
piroctone olamine (octopirox), a known agent with anti-seborrheic activity.

Therefore, in a preferred embodiment, the pharmaceutical compositions of the present invention also contain one or more of salicylic acid, hyaluronic acid, alpha-bisabolol, allantoin, zinc picolate. These compounds are preferably in the composition of the invention at a concentration range as follows (w/w %): about 0.1% to 5% salicylic acid; about 0.1% to about 10% hyaluronic acid; about 0.1% to 3% alpha-bisabolol; about 0.01% to about 1% zinc picolate; about 0.1% to 2% allantoin.

Other excipients that can be included in the compositions of the present invention include, but are not limited to, a viscosity-increasing agent, a surfactant, a stabilizing agent/preservative, a fragrance, a bioadhesive and a co-solubilizer.

Various topical delivery systems are known and can be used to administer a composition of the present invention, e.g., encapsulation in liposomes, microparticles, microcapsules, etc. In preferred embodiments, it is desirable to administer the pharmaceutical compositions of the invention locally to the area in need of treatment; this may be achieved by, for example, and not by way of limitation, topical application, e.g., in conjunction with a wound dressing after surgery, by means of a suppository, or by means of an implant, said implant being of a porous, non-porous, or gelatinous material, including membranes, such as sialastic membranes, or fibers.

For topical administration, the compositions can be formulated in the form of, e.g., an ointment, cream, transdermal patch, lotion, gel, shampoo, spray, aerosol, solution, emulsion, or other form well-known to one of skill in the art. See, e.g., Remington's Pharmaceutical Sciences and Introduction to Pharmaceutical Dosage Forms, 4th ed., Lea & Febiger, Philadelphia, Pa. (1985). For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon), or in a squeeze bottle. Moisturizers or humectants can also be added to pharmaceutical compositions and dosage forms if desired. Examples of such additional ingredients are well-known in the art.

In another embodiment, the composition of the invention can be delivered in a vesicle, in particular a liposome (see Langer, Science 249:1527 1533 (1990); Treat et al., in Liposomes in the Therapy of Infectious Disease and Cancer, Lopez-Berestein and Fidler (eds.), Liss, New York, pp. 353 365 (1989); Lopez Berestein, ibid., pp. 317 327; see generally ibid.). In preferred embodiments, the compositions of the present invention do not contain allergenic substances, derivatives from animal sources (such as lanolin, beeswax, animal fat), and certain preservatives (such as parabens, isothiazolones, phenol derivatives, and the like) which are often responsible for allergic contact dermatitis.

Examples of pharmaceutically acceptable salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also refers to a salt prepared from a compound having an acidic functional group, such as a carboxylic acid or sulfonic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis- or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N,-dimethyl-N-(2-hydroxyethyl)amine, or tri-(2-hydroxyethyl)amine; N-methyl-D-glucamine; and amino acids such as arginine, lysine, and the like.

In a preferred embodiment, the pharmaceutical compositions of the present invention are in the form of a cream, a gel, a lotion, a suspension, a spray, an ointment, or a foam. In another preferred embodiment, the compositions of the present invention do not contain substances derived from animal sources, such as lanolin, beeswax, animal fat, or preservatives, such as parabens, isothiazolones, phenol derivatives, and the like, which are often responsible for allergic contact dermatitis.

In preferred embodiments, the carriers (squalene, karitt butter, octyl palmitate and oenothera oil) are present in the composition at a range of about 10% to about 50% (w/w); the antioxidants (tocopherol acetate 0.5-5%; ascorbyl palmitate) are present in the composition at a range of about 0.01% to 0.1% (w/w).

The present invention is also directed to a method of treating or preventing an inflammatory condition of the mucosae, skin or the eye comprising topically administering to the site of the condition a composition comprising a proanthocyanidin, glycyrrhetinic acid and telmesteine, or pharmaceutically acceptable salts thereof, as the active ingredient, and a pharmaceutically acceptable carrier or excipient in an amount effective to treat or prevent such condition. In another embodiment, the present invention is directed to a method of treating or preventing atopic dermatitis, allergic contact dermatitis, seborrheic dermatitis, *xerosis*; psoriasis or atopia comprising topically administering a composition comprising proanthocyanidins, or a pharmaceutically acceptable salt thereof, as the active ingredient, and a pharmaceutically acceptable carrier or excipient to a subject in need of such treatment or prevention in an amount effective to treat or prevent atopic dermatitis, allergic contact dermatitis, seborrheic dermatitis, *xerosis*, psoriasis or atopia.

The present invention is also directed to a method of ameliorating at least one symptom of an inflammatory condition of the mucosae, skin or the eye comprising topically administering to the site of the condition a composition comprising a proanthocyanidin, glycyrrhetinic acid and telmesteine, or pharmaceutically acceptable salts thereof, as the active ingredient, and a pharmaceutically acceptable carrier or excipient in an amount effective to ameliorate at least one symptom associated with such condition.

More particularly, the compositions of the present invention are also useful as moisturizers and lenitives for sensitive, delicate skins or to treat or ameliorate allergic irritations caused by medicaments, detergents, solvents; treat, prevent or ameliorate erythema subsequent to excessive exposure to sun radiation. In other embodiments of the present invention, the compositions are useful in treating or ameliorating effects caused by insect bites, redness of various origin, post-shaving irritations, slight burns, cutaneous hyper-reactivity, as well as a normalizer after treatments of aesthetic medicine, such as skin peeling with glycolic acid or laser therapy.

More particularly, the compositions of the present invention are useful for the treatment or prevention of pathologies such as irritative and eczematous dermatitis, as moisturizers and lenitive for sensitive, delicate skins; in allergic irritations caused by medicaments, detergents, solvents; in erythema subsequent to excessive exposure to sun radiations; in case of insect bites, redness of various origin, post-shaving irritations, slight burns, cutaneous hyper-reactivity; as normalizers after treatments of aesthetic medicine, such as peeling with glycolic acid or laser therapy. Exemplary, non-limiting inflammatory conditions of the mucosae, skin or the eye include, but are not limited to, dermatitis conditions and skin impairments such as atopic dermatitis, contact dermatitis, allergic contact dermatitis, allergic dermatitis, seborrheic dermatitis, nummular dermatitis, chronic dermatitis of hands or feet, generalized exfoliative dermatitis, stasis dermatitis, neonatal dermatitis, pediatric dermatitis, localized scratch dermatitis, toxic/irritating contact eczema, allergic contact eczema, type I or type IV photoallergic contact eczema, contact urticaria, dyshidrosiform eczema, age-caused wrinkles, sun damage and itching.

Other conditions that can be treated by a composition of the present invention, include:

Psoriasis: psoriasis vulgaris, flaking eczema, psoriasis pustulosa, psoriasis arthropatica, psoriatic erythroderma;
Rosacea;
Photodermatosis: radiodermatitis acuta and chronica (UV and ionizing radiation therapy), chronic actinic dermatitis, photouticaria (uticaria solaris), polymorphic photodermatosis;
Prurigo: p. simplex acuta (strophulus, uticaria papulosa), subacuta, chronica;
Acne: acne vulgaris, juvenile and adult (acne with comedones, papulous, pustulous, nodose, i.e., nodular, nodulocystic acne), acne conglobata (special form: hidradenitis suppurativa), acne fulminans, acne tetrad, acne neonatorum, senile acne, mechanical acne forms (excoriated acne), acne cosmetica, folliculitis with superinfected acne (*Staphylococci*), occupation-related acne forms (for example chlorine acne);
Decubitis and Ulcus cruris;
Deficient ipoactive skin: localized scratch dermatitis rinophyma, ichthyosis, *xerosis*;
Perioral dermatits.

The precise dose to be employed in the composition will depend on the seriousness of the inflammatory condition, and should be decided according to the judgment of the practitioner and each patient's circumstances. In principle, however, a cream, lotion or ointment containing about 0.001% to about 20% proanthocyanidins (preferably in a complex with phospholipids), 0.01% to 20% glycyrrhetinic acid (preferably 1% to 2%) and 0.01% to 20% telmesteine (preferably 0.01% to 1%), or pharmaceutically acceptable salts thereof, in an oil base or an emulsion base, including oil-in-water type and water-in-oil type emulsions, applied two to three times or more daily, will be sufficient to provide an optimal therapeutic or preventive response. The treatment can be protracted until remission of symptoms, usually for at least 2 days, but preferably 5-10 days. More prolonged treatments are not contraindicated, considering the low, if any, toxicity of the components of the compositions of the invention. In preferred embodiments, the composition of the invention contains about 0.001% to about 20% proanthocyanidins in a complex with phospholipids, about 0.1% to about 10% proanthocyanidins in a complex with phospholipids, about 0.1% to about 5% proanthocyanidins in a complex with phospholipids, about 0.1% to about 2% proanthocyanidins in a complex with phospholipids, about 0.1% to about 1% proanthocyanidins in a complex with phospholipids, or about 0.5% to about 1% proanthocyanidins in a complex with phospholipids or a pharmaceutically acceptable salt thereof. In other preferred embodiments, the composition of the invention contains about 0.01%, 0.1%, 0.5%, 1%, 2%, 5%, 10%, 20% proanthocyanidins in a complex with phospholipids or a pharmaceutically acceptable salt thereof. In preferred embodiments, the composition of the invention contains about 0.01% to about 20% glycyrrhetinic acid, about 0.1% to about 10% glycyrrhetinic acid, about 0.1% to about 5% glycyrrhetinic acid, about 0.1% to about 2% glycyrrhetinic acid, about 0.1% to about 1% glycyrrhetinic acid, or about 0.5% to about 1% glycyrrhetinic acid or a pharmaceutically acceptable salt thereof. In other preferred embodiments, the composition of the invention contains about 0.01%, 0.1%, 0.5%, 1%, 2%, 5%, 10%, 20% glycyrrhetinic acid or a pharmaceutically acceptable salt thereof. In preferred embodiments, the composition of the invention contains about 0.01% to about 20% telmesteine, about 0.1% to about 10% telmesteine, about 0.1% to about 5% telmesteine, about 0.1% to about 2% telmesteine, about 0.1% to about 1% telmesteine, or about 0.5% to about 1% telmesteine or a pharmaceutically acceptable salt thereof. In other preferred embodiments, the composition of the invention contains about 0.01%, 0.1%, 0.5%, 1%, 2%, 5%, 10%, 20%, 25% telmesteine or a pharmaceutically acceptable salt thereof.

In alternative embodiments, other active ingredients can be co-administered to treat or prevent an inflammatory condition of the mucosae, skin or the eye in the same composition with a composition of the present invention or in a separate composition. Preferably, the additional active ingredients are co-administered in a separate pharmaceutical composition. In other embodiments, the additional active ingredients are co-administered in a separate composition at the same time or a later time as administration of a composition of the present invention. Examples of other topical agents include, but are not limited to emolliments, salicyclic acid, coal tar, anthralins, topical steroids, topical corticosteroids (e.g., difloroasone diacetate, clobetasol propionate, halobetasol propionate, betamethasone dipropionate, fluocinonide, halcinonide desoximetasone, triamcinolone, fluticasone propionate, fluocinolone acetonide, flurandrenolide, mometasone furoate, betamethosone, fluticasone propionate, fluocinolone acetonide, aclometasome dipropionate, desonide and hydrocortisone), topical vitamin D3 analogs (e.g., calcipotriene), topical retinoids (e.g., tazarotene). In certain embodiments, another agent is a systemically administered agent. Examples of agents administered systemically include, but are not limited to, systemic corticosteroids (e.g., triamcinalone), folic acid antagonists (e.g., methotrexate), retinoids (e.g., acetretin) and cyclosporine.

The present invention also provides a pharmaceutical pack or kit comprising one or more containers, e.g., a flexible packet, vial, ampoule, bottle and the like, filled with one or more of the ingredients of the compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In a preferred embodiment, the compositions of the present invention can be presented as single- or multi-dose forms in a flexible packet. Preferably, the compositions of the present invention are packaged in the concentrated form in flexible packets with a dose of from about 10 to about 30 ml per packet that can be diluted with water to create about 40-60 ml of product for use by the patient.

The following series of examples are presented by way of illustration and not by way of limitation on the scope of the present invention.

5. EXAMPLES

Example 1

| | |
|---|---|
| Complexes of proanthocyanidins from *Vitis vinifera* with phospholipids | 0.1% |
| Glycyrrhetinic acid | 0.8% |
| Telmesteine | 0.1% |
| Octyl palmitate | 7.0% |

-continued

| | |
|---|---|
| Pentylene glycol | 5.0% |
| Karite butter | 4.0% |
| Arachidyl alcogol, behenyl alcohol, C 12-20 alkylglucoside | 4.0% |
| Glyceryl stearate and glyceryl (100) OE stearate | 3.0% |
| Oenothera oil | 2.0% |
| Capriloyl glycine | 1.5% |
| Bisabolol | 1.2% |
| Vitamin E acetate | 1.0% |
| Carbomer | 0.7% |
| Octyl glycerin | 0.6% |
| Salicylic acid | 0.5% |
| Octopirox | 0.5% |
| Sodium hydroxide | 0.387% |
| Allantoin | 0.35% |
| Zinc pidolate | 0.1% |
| EDTA disodium salt | 0.08% |
| Ascorbyl palmitate | 0.05% |
| Propyl gallage | 0.02% |
| Water | 65.013% |
| Total | 100.0% |

Example 2

| | |
|---|---|
| Complexes of proanthocyanidins from *Vitis vinifera* with phospholipids | 0.1% |
| Glycyrrhetinic acid | 0.8% |
| Telmesteine | 0.1% |
| Octyl palmitate | 7.0% |
| Pentylene glycol | 5.0% |
| Karite butter | 4.0% |
| Arachidyl alcogol, behenyl alcohol, C 12-20 alkylglucoside | 4.0% |
| Glyceryl stearate and glyceryl (100) OE stearate | 3.0% |
| Squalene | 2.0% |
| Oenothera oil | 2.0% |
| Capriloyl glycine | 1.5% |
| Bisabolol | 1.2% |
| Vitamin E acetate | 1.0% |
| Carbomer | 0.7% |
| Octyl glycerin | 0.6% |
| Sodium hydroxide | 0.387% |
| Zinc pidolate | 0.1% |
| EDTA disodium salt | 0.08% |
| Ascorbyl palmitate | 0.05% |
| Propyl gallage | 0.02% |
| Water | 66.013% |
| Total | 100.0% |

Example 3

| | |
|---|---|
| Complexes of proanthocyanidins from *Vitis vinifera* with phospholipids | 0.1% |
| Glycyrrhetinic acid | 0.8% |
| Telmesteine | 0.01% |
| Dub po | 7.0% |
| Hydrolite-5 | 5.0% |
| Karité butter | 4.0% |
| Montanov 202 | 4.0% |
| Arlacel 165 | 3.0% |
| Squalene ex | 2.0% |
| Oenothera oil | 2.0% |
| Lipacide C8G | 1.5% |
| Bisabolol | 1.2% |
| Vitamin E acetate | 1.0% |
| Carbopol ultrex 10 | 0.7% |
| Sensiva SC 50 | 0.6% |

-continued

| | |
|---|---|
| Octopirox | 0.5% |
| Sodium hydroxide drops P.P.A. | 0.387% |
| Allantoin | 0.35% |
| Nipaguard DMDMH | 0.3% |
| Zincidone | 0.1% |
| EDTA disodium salt | 0.08% |
| Ascorbyl palmitate | 0.05% |
| Propyl gallage | 0.02% |
| Water | 65.303% |
| Total | 100.0% |

Example 4

| | |
|---|---|
| Complexes of proanthocyanidins from *Vitis vinifera* with phospholipids | 0.1% |
| Glycyrrhetinic acid | 0.8% |
| Telmesteine | 0.01% |
| Dub po | 7.0% |
| Hydrolite-5 | 5.0% |
| Karité butter | 4.0% |
| Montanov 202 | 4.0% |
| Arlacel 165 | 3.0% |
| Squalene ex | 2.0% |
| Oenothera oil | 2.0% |
| Lipacide C8G | 1.5% |
| Bisabolol | 1.2% |
| Vitamin E acetate | 1.0% |
| Carbopol ultrex 10 | 0.7% |
| Sensiva SC 50 | 0.6% |
| Salicylic acid | 0.5% |
| Octopirox | 0.5% |
| Sodium hydroxide drops P.P.A. | 0.465% |
| Allantoin | 0.35% |
| Nipaguard DMDMH | 0.3% |
| Zincidone | 0.1% |
| EDTA disodium salt | 0.08% |
| Ascorbyl palmitate | 0.05% |
| Propyl gallage | 0.02% |
| Water | 64.725% |
| Total | 100.0% |

Example 5

| | |
|---|---|
| Complexes of proanthocyanidins from *Vitis vinifera* with phospholipids | 0.1% |
| Glycyrrhetinic acid | 0.8% |
| Telmesteine | 0.1% |
| Dub po | 7.0% |
| Hydrolite-5 | 5.0% |
| Karité butter | 4.0% |
| Montanov 202 | 4.0% |
| Arlacel 165 | 3.0% |
| Squalene | 2.0% |
| Oenothera oil | 1.5% |
| Lipacide C8G | 1.2% |
| Bisabolol | 1.0% |
| Vitamin E acetate | 0.7% |
| Carbopol ultrex 10 | 0.6% |
| Sensiva SC 50 | 0.5% |
| Octopirox | 0.5% |
| Sodium hydroxide drops P.P.A. | 0.387% |
| Allantoin | 0.35% |
| Nipaguard DMDMH | 0.3% |
| Zincidone | 0.1% |
| EDTA disodium salt | 0.08% |

-continued

| | |
|---|---|
| Ascorbyl palmitate | 0.05% |
| Hyaluronic acid sodium salt | 0.03% |
| Propyl gallage | 0.02% |
| Water | 65.273% |
| Total | 100.0% |

Example 6

| | |
|---|---|
| Complexes of proanthocyanidins from *Vitis vinifera* with phospholipids | 0.1% |
| Glycyrrhetinic acid | 2.0% |
| Telmesteine | 0.01% |
| Ethylhexyl palmitate | 9.0% |
| Butyrospermum parkii | 6.0% |
| Pentylene glycol | 5.0% |
| Butylene glycol | 3.0% |
| PEG-100 stearate | 1.5% |
| Glyceryl stearate | 1.5% |
| Capryloyl glycine | 1.5% |
| Arachidyl glucoside | 1.36% |
| Arachidyl alcohol | 1.32% |
| Behenyl alcohol | 1.32% |
| Bisabolol | 1.2% |
| Tocopheryl acetate | 1.0% |
| Carbomer | 0.7% |
| Ethylhexyl glycerin | 0.6% |
| Piroctone olamine | 0.5% |
| Sodium hydroxide | 0.387% |
| Allantoin | 0.35% |
| DMDM hydratoin | 0.3% |
| Sodium hyaluronate | 0.2% |
| Disodium EDTA | 0.08% |
| Tetrahexyidecyl ascorbate | 0.05% |
| Propyl gallage | 0.02% |
| Water | 61.003% |
| Total | 100.0% |

Example 7

| | |
|---|---|
| Complexes of proanthocyanidins from *Vitis vinifera* with phospholipids | 0.1% |
| Glycyrrhetinic acid | 2.0% |
| Telmesteine | 0.01% |
| Ethylhexyl palmitate | 9.0% |
| Butyrospermum parkii | 6.0% |
| Pentylene glycol | 5.0% |
| Butylene glycol | 3.0% |
| PEG-100 stearate | 1.5% |
| Glyceryl stearate | 1.5% |
| Capryloyl glycine | 1.5% |
| Arachidyl glucoside | 1.36% |
| Arachidyl alcohol | 1.32% |
| Behenyl alcohol | 1.32% |
| Bisabolol | 1.2% |
| Salicylic acid | 1.0% |
| Tocopheryl acetate | 1.0% |
| Sodium hydroxide | 0.785% |
| Carbomer | 0.7% |
| Ethylhexyl glycerin | 0.6% |
| Piroctone olamina | 0.5% |
| Allantoin | 0.35% |
| DMDM hydratoin | 0.3% |
| Disodium EDTA | 0.08% |
| Tetrahexyidecyl ascorbate | 0.05% |
| Propyl gallage | 0.02% |

-continued

| | |
|---|---|
| Water | 59.805% |
| Total | 100.0% |

Example 8

| | |
|---|---|
| Complexes of proanthocyanidins from *Vitis vinifera* with phospholipids | 0.1% |
| Glycyrrhetinic acid | 2.0% |
| Telmesteine | 0.01% |
| Ethylhexyl palmitate | 9.0% |
| Butyrospermum parkii | 6.0% |
| Pentylene glycol | 5.0% |
| Butylene glycol | 3.0% |
| PEG-100 stearate | 1.5% |
| Glyceryl stearate | 1.5% |
| Capryloyl glycine | 1.5% |
| Arachidyl glucoside | 1.36% |
| Arachidyl alcohol | 1.32% |
| Behenyl alcohol | 1.32% |
| Bisabolol | 1.2% |
| Tocopheryl acetate | 1.0% |
| Carbomer | 0.7% |
| Ethylhexyl glycerin | 0.6% |
| Piroctone olamine | 0.5% |
| Sodium hydroxide | 0.387% |
| Allantoin | 0.35% |
| DMDM hydratoin | 0.3% |
| Sodium hyaluronate | 0.1% |
| Disodium EDTA | 0.08% |
| Tetrahexyidecyl ascorbate | 0.05% |
| Propyl gallage | 0.02% |
| Water | 61.103% |
| Total | 100.0% |

Example 9

MAS063/E1

| Name | Percent |
|---|---|
| Water | 55.4779 |
| Ethylhexyl Palmitate | 9.0 |
| Butyrospermum Parkii | 6.0 |
| Pentylene Glycol | 5.0 |
| Arachidyl Alcohol, Behenyl Alcohol, Arachidyl Glucoside | 4.0 |
| Acrylates Copolymer, Water | 4.0 |
| Glyceryl Stearate, Peg-100 Stearate | 3.0 |
| Butylene Glycol | 3.0 |
| Glycyrrhetinic Acid | 2.0 |
| Capryloyl Glycine | 1.5 |
| Bisabolol | 1.2 |
| Tocopheryl Acetate | 1.0 |
| Phenoxyethanol | 0.9 |
| Carbomer | 0.7 |
| Ethylhexylglycerine | 0.6 |
| Piroctone Olamine | 0.5 |
| Sodium Hydroxide | 0.497 |
| Allantoin | 0.35 |
| Complexes of proanthocyanidins from *Vitis vinifera* with phospholipids | 0.30 |
| Sodium Hyaluronate | 0.1 |
| Disodium EDTA | 0.8 |
| Tetrahexyldecyl Ascorbate | 0.05 |
| Ammonium Acryloyldimethyl Taurate/Vp Copolymer | 0.015 |
| Telmesteine | 0.01 |

-continued

MAS063/E1

| Name | Percent |
|---|---|
| Propyl Gallate | 0.0001 |
| TOTAL | 100.00 |

Example 10

MAS060d

| Name | Percent |
|---|---|
| Water | 60.433 |
| Ethylhexyl Palmitate | 7.0 |
| Pentylene Glycol | 5.0 |
| Butyrospermum Parkii | 4.0 |
| Arachidyl Alcohol, Behenyl Alcohol, Arachidyl Glucoside | 4.0 |
| Glyceryl Stearate, Peg-100 Stearate | 3.0 |
| Butylene Glycol | 3.0 |
| Oenothera Biennis | 2.0 |
| Glycyrrhetinic Acid | 2.0 |
| Olea Europaea | 2.0 |
| Capryloyl Glycine | 1.5 |
| Bisabolol | 1.2 |
| Tocopheryl Acetate | 1.0 |
| Carbomer | 0.7 |
| Ethylhexylglycerine | 0.6 |
| Piroctone Olamine | 0.5 |
| Sodium Hydroxide | 0.387 |
| Allantoin | 0.35 |
| Dmdm Hydantoin | 0.3 |
| Complexes of proanthocyanidins from *Vitis vinifera* with phospholipids | 0.1 |
| Sodium Hyaluronate | 0.1 |
| Disodium EDTA | 0.8 |
| Propyl Gallate | 0.02 |
| Telmesteine | 0.01 |
| TOTAL | 100.00 |

Example 11

MAS016D

| Name | Percent |
|---|---|
| Water | 64.433 |
| Ethylhexyl Palmitate | 7.0 |
| Pentylene Glycol | 5.0 |
| Butyrospermum Parkii | 4.0 |
| Arachidyl Alcohol, Behenyl Alcohol, Arachidyl Glucoside | 4.0 |
| Glyceryl Stearate, Peg-100 Stearate | 3.0 |
| Squalene | 2.0 |
| Oenothera Biennis | 2.0 |
| Capryloyl Glycine | 1.5 |
| Bisabolol | 1.2 |
| Tocopheryl Acetate | 1.0 |
| Glycyrrhetinic Acid | 0.8 |
| Carbomer | 0.7 |
| Ethylhexylglycerine | 0.6 |
| Piroctone Olamine | 0.5 |
| Sodium Hydroxide | 0.387 |
| Allantoin | 0.35 |
| Zinc Pca | 0.1 |

-continued

MAS016D

| Name | Percent |
|---|---|
| Proanthocyanidins from *Vitis vinifera* | 0.1 |
| Disodium EDTA | 0.8 |
| Ascorbyl Palmitate | 0.5 |
| Propyl Gallate | 0.02 |
| TELMESTEINE | 0.01 |
| TOTAL | 100.00 |

Example 12

MAS017D

| Name | Percent |
|---|---|
| Water | 64.133 |
| Ethylhexyl Palmitate | 7.0 |
| Pentylene Glycol | 5.0 |
| Butyrospermum Parkii | 4.0 |
| Arachidyl Alcohol, Behenyl Alcohol, Arachidyl Glucoside | 4.0 |
| Glyceryl Stearate, Peg-100 Stearate | 3.0 |
| Squalene | 2.0 |
| Oenothera Biennis | 2.0 |
| Capryloyl Glycine | 1.5 |
| Bisabolol | 1.2 |
| Tocopheryl Acetate | 1.0 |
| Glycyrrhetinic Acid | 0.8 |
| Carbomer | 0.7 |
| Ethylhexylglycerine | 0.6 |
| Piroctone Olamine | 0.5 |
| Sodium Hydroxide | 0.387 |
| Allantoin | 0.35 |
| Dmdm Hydantoin | 0.3 |
| Zinc Pca | 0.1 |
| Proanthocyanidins from *Vitis vinifera* | 0.1 |
| Disodium EDTA | 0.8 |
| Ascorbyl Palmitate | 0.5 |
| Propyl Gallate | 0.02 |
| Telmesteine | 0.01 |
| TOTAL | 100.00 |

Example 13

MAS063/A1

| Name | Percent |
|---|---|
| Water | 55.379 |
| Ethylhexyl Palmitate | 9.0 |
| Butyrospermum Parkii | 6.0 |
| Pentylene Glycol | 5.0 |
| Arachidyl Alcohol, Behenyl Alcohol, Arachidyl Glucoside | 4.0 |
| Acrylates Copolymer, Water | 4.0 |
| Glyceryl Stearate, Peg-100 Stearate | 3.0 |
| Butylene Glycol | 3.0 |
| Glycyrrhetinic Acid | 2.0 |
| Capryloyl Glycine | 1.5 |
| Bisabolol | 1.2 |
| Tocopheryl Acetate | 1.0 |
| Phenoxyethanol | 0.9 |
| Carbomer | 0.7 |

MAS063/A1

| Name | Percent |
| --- | --- |
| Ethylhexylglycerine | 0.6 |
| Piroctone Olamine | 0.5 |
| Sodium Hydroxide | 0.497 |
| Allantoin | 0.35 |
| Sodium Dehydroacetate | 0.3 |
| Sodium Hyaluronate | 0.1 |
| Complexes of proanthocyanidins from *Vitis vinifera* with phospholipids | 0.1 |
| Disodium EDTA | 0.8 |
| Tetrahexyldecyl Ascorbate | 0.05 |
| Ammonium Acryloyldimethyl Taurate/Vp Copolymer | 0.015 |
| Telmesteine | 0.01 |
| Propyl Gallate | 0.0001 |
| TOTAL | 100.00 |

Example 14

MAS023D

| Name | Percent |
| --- | --- |
| Water | 60.383 |
| Ethylhexyl Palmitate | 7.0 |
| Pentylene Glycol | 5.0 |
| Butyrospermum Parkii | 4.0 |
| Arachidyl Alcohol, Behenyl Alcohol, Arachidyl Glucoside | 4.0 |
| Glyceryl Stearate, Peg-100 Stearate | 3.0 |
| Butylene Glycol | 3.0 |
| Oenothera Biennis | 2.0 |
| Glycyrrhetinic Acid | 2.0 |
| Olea Europaea | 2.0 |
| Capryloyl Glycine | 1.5 |
| Bisabolol | 1.2 |
| Tocopheryl Acetate | 1.0 |
| Carbomer | 0.7 |
| Ethylhexylglycerine | 0.6 |
| Piroctone Olamine | 0.5 |
| Sodium Hydroxide | 0.387 |
| Allantoin | 0.35 |
| Dmdm Hydantoin | 0.3 |
| Proanthocyanidins from *Vitis vinifera* | 0.1 |
| Sodium Hyaluronate | 0.1 |
| Disodium EDTA | 0.8 |
| Ascorbyl Palmitate | 0.05 |
| Propyl Gallate | 0.02 |
| Telmesteine | 0.01 |
| TOTAL | 100.00 |

Example 15

MAS063D

| Name | Percent |
| --- | --- |
| Water | 60.383 |
| Ethylhexyl Palmitate | 9.0 |
| Butyrospermum Parkii | 6.0 |
| Pentylene Glycol | 5.0 |
| Arachidyl Alcohol, Behenyl Alcohol, Arachidyl Glucoside | 4.0 |
| Glyceryl Stearate, Peg-100 Stearate | 3.0 |
| Butylene Glycol | 3.0 |
| Glycyrrhetinic Acid | 2.0 |
| Capryloyl Glycine | 1.5 |
| Bisabolol | 1.2 |
| Tocopheryl Acetate | 1.0 |
| Carbomer | 0.7 |
| Ethylhexylglycerine | 0.6 |
| Piroctone Olamine | 0.5 |
| Sodium Hydroxide | 0.387 |
| Allantoin | 0.35 |
| Dmdm Hydantoin | 0.3 |
| Proanthocyanidins from *Vitis vinifera* | 0.1 |
| Sodium Hyaluronate | 0.1 |
| Disodium EDTA | 0.8 |
| Tetrahexyldecyl Ascorbate | 0.05 |
| Propyl Gallate | 0.02 |
| Telmesteine | 0.01 |
| TOTAL | 100.00 |

Example 16

MAS065D

| Name | Percent |
| --- | --- |
| Water | 61.003 |
| Ethylhexyl Palmitate | 9.0 |
| Bytyrospermum Parkii | 6.0 |
| Pentylene Glycol | 5.0 |
| Arachidyl Alcogol, Behenyl Alcogol, Arachidyl Glucoside | 4.0 |
| Glyceryl Stearate, Peg-100 Stearate | 3.0 |
| Butylene Glycol | 3.0 |
| Glycyrrhetinic Acid | 2.0 |
| Capryloyl Glycine | 1.5 |
| Bisabolol | 1.2 |
| Tocopheryl Acetate | 1.0 |
| Carbomer | 0.7 |
| Ethylhexylglycerin | 0.6 |
| Piroctone Olamine | 0.5 |
| Sodium Hydroxide | 0.387 |
| Allantoin | 0.35 |
| Dmdm Hydantoin | 0.3 |
| Sodium Hyaluronate | 0.2 |
| Proanthocyanidins from *Vitis vinifera* | 0.1 |
| Disodium EDTA | 0.08 |
| Tetrahexyldecyl Ascorbate | 0.05 |
| Propyl Gallate | 0.02 |
| Telmesteine | 0.01 |
| TOTAL | 100.00 |

Example 17

MAS019D

| Name | Percent |
| --- | --- |
| Water | 65.003 |
| Ethylhexyl Palmitate | 7.0 |

MAS019D

| Name | Percent |
| --- | --- |
| Pentylene Glycol | 5.0 |
| Bytyrospermum Parkii | 4.0 |
| Arachidyl Alcogol, Behenyl Alcogol, Arachidyl Glucoside | 4.0 |
| Glyceryl Stearate, Peg-100 Stearate | 3.0 |
| Squalene | 2.0 |
| Oenothera Biennis | 2.0 |
| Capryloyl Glycine | 1.5 |
| Bisabolol | 1.2 |
| Tocopheryl Acetate | 1.0 |
| Glycyrrhetinic Acid | 0.8 |
| Carbomer | 0.7 |
| Ethylhexylglycerin | 0.6 |
| Piroctone Olamine | 0.5 |
| Sodium Hydroxide | 0.387 |
| Allantoin | 0.35 |
| Dmdm Hydantoin | 0.3 |
| Zinc Pca | 0.1 |
| Proanthocyanidins from *Vitis vinifera* | 0.1 |
| Disodium EDTA | 0.08 |
| Ascorbyl Palmitate | 0.05 |
| Sodium Hyaluronate | 0.3 |
| Propyl Gallate | 0.02 |
| Telmesteine | 0.01 |
| TOTAL | 100.00 |

Example 18

MAS025D

| Name | Percent |
| --- | --- |
| Water | 61.003 |
| Ethylhexyl Palmitate | 7.0 |
| Pentylene Glycol | 5.0 |
| Butyrospermum Parkii | 4.0 |
| Arachidyl Alcohol, Behenyl Alcohol, Arachidyl Glucoside | 4.0 |
| Glyceryl Stearate, Peg-100 Stearate | 3.0 |
| Butylene Glycol | 3.0 |
| Oenothera Biennis | 2.0 |
| Glycyrrhetinic Acid | 2.0 |
| Olea Europaea | 2.0 |
| Capryloyl Glycine | 1.5 |
| Bisabolol | 1.2 |
| Tocopheryl Acetate | 1.0 |
| Carbomer | 0.7 |
| Ethylhexylglycerine | 0.6 |
| Piroctone Olamine | 0.5 |
| Sodium Hydroxide | 0.387 |
| Allantoin | 0.35 |
| Dmdm Hydantoin | 0.3 |
| Sodium Hyaluronate | 0.2 |
| Proanthocyanidins from *Vitis vinifera* | 0.1 |
| Disodium EDTA | 0.08 |
| Ascorbyl Palmitate | 0.05 |
| Propyl Gallate | 0.02 |
| Telmesteine | 0.01 |
| TOTAL | 100.00 |

Example 19

MAS062D

| Name | Percent |
| --- | --- |
| Water | 61.053 |
| Ethylhexyl Palmitate | 7.0 |
| Pentylene Glycol | 5.0 |
| Butyrospermum Parkii | 4.0 |
| Arachidyl Alcohol, Behenyl Alcohol, Arachidyl Glucoside | 4.0 |
| Glyceryl Stearate, Peg-100 Stearate | 3.0 |
| Butylene Glycol | 3.0 |
| Oenothera Biennis | 2.0 |
| Glycyrrhetinic Acid | 2.0 |
| Olea Europaea | 2.0 |
| Capryloyl Glycine | 1.5 |
| Bisabolol | 1.2 |
| Tocopheryl Acetate | 1.0 |
| Carbomer | 0.7 |
| Ethylhexylglycerine | 0.6 |
| Piroctone Olamine | 0.5 |
| Sodium Hydroxide | 0.387 |
| Allantoin | 0.35 |
| Dmdm Hydantoin | 0.3 |
| Sodium Hyaluronate | 0.2 |
| Proanthocyanidins from *Vitis vinifera* | 0.1 |
| Disodium EDTA | 0.08 |
| Propyl Gallate | 0.02 |
| Telmesteine | 0.01 |
| TOTAL | 100.00 |

Example 20

MAS065A1

| Name | Percent |
| --- | --- |
| Water | 56.035 |
| Ethylhexyl Palmitate | 9.0 |
| Butyrospermum Parkii | 6.0 |
| Pentylene Glycol | 5.0 |
| Arachidyl Alcohol, Behenyl Alcohol, Arachidyl Glucoside | 4.0 |
| Acrylates Copolyer, Water | 4.0 |
| Glyceryl Stearate, Peg-100 Stearate | 3.0 |
| Butylene Glycol | 3.0 |
| Glycyrrhetinic Acid | 2.0 |
| Capryloyl Glycine | 1.5 |
| Bisabolol | 1.2 |
| Tocopheryl Acetate | 1.0 |
| Phenoxyethanol | 0.9 |
| Carbomer | 0.7 |
| Ethylhexylglycerine | 0.6 |
| Piroctone Olamine | 0.5 |
| Sodium Hydroxide | 0.44 |
| Allantoin | 0.35 |
| Sodium Dehydroacetate | 0.3 |
| Sodium Hyaluronate | 0.2 |
| Complexes of proanthocyanidins from *Vitis vinifera* with phospholipids | 0.1 |
| Disodium EDTA | 0.08 |
| Tetrahexyldecyl Ascorbate | 0.05 |
| Propyl Gallate | 0.02 |
| Ammonium Acryloyldimethyl Taurate/Vp Copolymer | 0.015 |
| Telmesteine | 0.01 |
| TOTAL | 100.00 |

Example 21

MAS063D

| Name | Percent |
|---|---|
| Water | 59.805 |
| Ethylhexyl Palmitate | 9.0 |
| Bytyrospermum Parkii | 6.0 |
| Pentylene Glycol | 5.0 |
| Arachidyl Alcogol, Behenyl Alcogol, Arachidyl Glucoside | 4.0 |
| Glyceryl Stearate, Peg-100 Stearate | 3.0 |
| Butylene Glycol | 3.0 |
| Glycyrrhetinic Acid | 2.0 |
| Capryloyl Glycine | 1.5 |
| Bisabolol | 1.2 |
| Tocopheryl Acetate | 1.0 |
| Salicylic Acid | 1.0 |
| Sodium Hydroxide | 0.785 |
| Carbomer | 0.7 |
| Ethylhexylglycerin | 0.6 |
| Piroctone Olamine | 0.5 |
| Allantoin | 0.35 |
| Dmdm Hydantoin | 0.3 |
| Proanthocyanidins from *Vitis vinifera* | 0.1 |
| Disodium EDTA | 0.08 |
| Tetrahexyldecyl Ascorbate | 0.05 |
| Propyl Gallate | 0.02 |
| Telmesteine | 0.01 |
| TOTAL | 100.00 |

Example 22

MAS018D

| Name | Percent |
|---|---|
| Water | 64.725 |
| Ethylhexyl Palmitate | 7.0 |
| Pentylene Glycol | 5.0 |
| Bytyrospermum Parkii | 4.0 |
| Arachidyl Alcogol, Behenyl Alcogol, Arachidyl Glucoside | 4.0 |
| Glyceryl Stearate, Peg-100 Stearate | 3.0 |
| Squalene | 2.0 |
| Oenothera Biennis | 2.0 |
| Capryloyl Glycine | 1.5 |
| Bisabolol | 1.2 |
| Tocopheryl Acetate | 1.0 |
| Glycyrrhetinic Acid | 0.8 |
| Carbomer | 0.7 |
| Ethylhexylglycerin | 0.6 |
| Salicylic Acid | 0.5 |
| Piroctone Olamine | 0.5 |
| Sodium Hydroxide | 0.465 |
| Allantoin | 0.35 |
| Dmdm Hydantoin | 0.3 |
| Zinc Pca | 0.1 |
| Complexes of proanthocyanidins from *Vitis vinifera* with phospholipids | 0.1 |
| Disodium EDTA | 0.08 |
| Ascorbyl Palmitate | 0.05 |
| Propyl Gallate | 0.02 |
| Telmesteine | 0.01 |
| TOTAL | 100.00 |

Example 23

MAS024D

| Name | Percent |
|---|---|
| Wter | 59.805 |
| Ethylhexyl Palmitate | 7.0 |
| Pentylene Glycol | 5.0 |
| Butyrospermum Park Ii | 4.0 |
| Arachidyl Alcohol, Behenyl Alcohol, Arachidyl Glucoside | 4.0 |
| Glyceryl Stearate, Peg-100 Stearate | 3.0 |
| Butylene Glycol | 3.0 |
| Oenothera Biennis | 2.0 |
| Glycyrrhetinic Acid | 2.0 |
| Olea Europaea | 2.0 |
| Capryloyl Glycine | 1.5 |
| Bisabolol | 1.2 |
| Tocopheryl Acetate | 1.0 |
| Salicylic Acid | 1.0 |
| Sodium Hydroxide | 0.785 |
| Carbomer | 0.7 |
| Ethylhexylglycerine | 0.6 |
| Piroctone Olamine | 0.5 |
| Allantoin | 0.35 |
| Dmdm Hydantoin | 0.3 |
| Complexes of proanthocyanidins from *Vitis vinifera* with phospholipids | 0.1 |
| Disodium EDTA | 0.08 |
| Ascorbyl Palmitate | 0.05 |
| Propyl Gallate | 0.02 |
| Telmesteine | 0.01 |
| TOTAL | 100.00 |

Example 24

MAS061D

| Name | Percent |
|---|---|
| Water | 59.855 |
| Ethylhexyl Palmitate | 7.0 |
| Pentylene Glycol | 5.0 |
| Butyrospermum Parkii | 4.0 |
| Arachidyl Alcohol, Behenyl Alcohol, Arachidyl Glucoside | 4.0 |
| Glyceryl Stearate, Peg-100 Stearate | 3.0 |
| Butylene Glycol | 3.0 |
| Oenothera Biennis | 2.0 |
| Glycyrrhetinic Acid | 2.0 |
| Olea Europaea | 2.0 |
| Capryloyl Glycine | 1.5 |
| BISABOLOL | 1.2 |
| Tocopheryl Acetate | 1.0 |
| Salicylic Acid | 1.0 |
| Sodium Hydroxide | 0.785 |
| Carbomer | 0.7 |
| Ethylhexylglycerine | 0.6 |
| Piroctone Olamine | 0.5 |
| Allantoin | 0.35 |
| Dmdm Hydantoin | 0.3 |
| Complexes of proanthocyanidins from *Vitis vinifera* with phospholipids | 0.1 |
| Disodium EDTA | 0.08 |
| Propyl Gallate | 0.02 |
| Telmesteine | 0.01 |
| TOTAL | 100.00 |

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled. Such modifications are intended to fall within the scope of the appended claims.

All references, patent and non-patent, cited herein are incorporated herein by reference in their entireties and for all purposes to the same extent as if each individual publication or patent or patent application was specifically and individually indicated to be incorporated by reference in its entirety for all purposes.

What is claimed is:

1. A composition comprising a proanthocyanidin, glycyrrhetinic acid, telmesteine, salicylic acid and a pharmaceutically acceptable carrier.

2. A composition comprising a proanthocyanidin, glycyrrhetinic acid, telmesteine, hyaluronic acid and a pharmaceutically acceptable carrier.

3. The composition according to claim 1 or claim 2, wherein the composition is in the form of a cream, a gel, a lotion, a suspension, a spray, an ointment, or a foam.

4. The composition according to claim 1 or claim 2, wherein the composition further comprises a wetting agent.

5. The composition according to claim 1 or claim 2, wherein the composition further comprises one or more of squalene, karite butter, octyl palmitate, or oenothera oil.

6. The composition according to claim 1 or claim 2, wherein the composition further comprises a tocopherol, ascorbic acid, or an ester thereof.

7. The composition according to claim 6, wherein the composition further comprises tocopherol acetate, ascorbyl palmitate or tetrapalmitate.

8. The composition according to claim 1 or claim 2, wherein the composition further comprises at least one compound selected from the group consisting of alpha-bisabolol, zinc picolate, allantoin, and piroctone olamine.

9. The composition according to claim 1 or claim 2, wherein the proanthocyanidin is in a complex with phospholipids.

10. The composition according to claim 9, wherein the proanthocyanidin in complex with phospholipids is present in the composition at a concentration range of about 0.01% to about 1%.

11. The composition according to claim 1 or claim 2, wherein glycyrrhetinic acid is present in the composition at a concentration range of about 0.1% to about 5%.

12. The composition according to claim 1 or claim 2, wherein telmesteine is present in the composition at a concentration range of about 0.01% to about 1%.

13. A composition comprising about 0.1% proanthocyanidins in a complex with phospholipids, about 0.8% glycyrrhetinic acid, about 0.1% telmesteine, about 7.0% octyl palmitate, about 5.0% pentylene glycol, about 4.0% karite butter, about 4.0% arachidyl alcogol, behenyl alcohol, C 12-20 alkylglucoside, about 3.0% glyceryl stearate and glyceryl (100) stearate, about 2.0% oenothera oil, about 1.5% vapriloyl glycine, about 1.2% bisabolol, about 1.0% vitamin E acetate, about 0.7% carbomer, about 0.6% octyl glycerin, about 0.5% salicylic acid, about 0.5% octopirox, about 0.387% sodium hydroxide, about 0.35% allantoin, about 0.1% zinc picolate, about 0.08% EDTA disodium salt, about 0.05% ascorbyl palmitate, about 0.02% propyl gallage, and about 65.013% water.

14. A method for treating atopic dermatitis, allergic contact dermatitis, seborrheic dermatitis, *xerosis*; psoriasis, radiodermatitis acuta and chronica (UV and ionizing radiation therapy) or atopia comprising topically administering a composition comprising proanthocyanidins, glycyrrhetinic acid and telmesteine to a subject in need of such treatment in an amount effective to treat atopic dermatitis, allergic contact dermatitis, seborrheic dermatitis, *xerosis*, psoriasis or atopia.

15. The method according to claim 14, wherein the proanthocyanidins are in a complex with phospholipids.

16. The method according to claim 14, wherein the composition further comprises one or more agents selected from the group consisting of a wetting agent, salicylic acid, allantoin, hyaluronic acid, zinc pidolate, alpha-bisabolol, and piroctone olamine.

17. A method for treating an inflammatory condition of the mucosae, skin or the eye comprising topically administering a composition comprising proanthocyanidin, glycyrrhetinic acid and telmesteine to a subject in need of such treatment in an amount effective to treat the inflammatory condition.

18. The method according to claim 17, wherein the composition further comprises one or more agents selected from the group consisting of a wetting agent, salicylic acid, allantoin, hyaluronic acid, zinc picolate, alpha-bisabolol, and piroctone olamine.

19. The method according to claim 17, wherein the proanthocyanidins are in a complex with phospholipids.

20. The method according to claim 17, wherein the inflammatory condition is selected from the group consisting of atopic dermatitis, allergic contact dermatitis, seborrheic dermatitis, radiation dermatitis, *xerosis*; psoriasis and atopia.

21. The method according to claim 17, wherein the administration is vaginal, rectal, buccal or in the eye.

22. The method according to claim 17, wherein the inflammatory condition is selected from the group consisting of dermatitis conditions and skin impairments such as atopic dermatitis, contact dermatitis, allergic contact dermatitis, allergic dermatitis, seborrheic dermatitis, nummular dermatitis, chronic dermatitis of hands or feet, generalized exfoliative dermatitis, stasis dermatitis, neonatal dermatitis, pediatric dermatitis, localized scratch dermatitis, toxic/irritating contact eczema, allergic contact eczema, type I or type IV photoallergic contact eczema, contact urticaria, dyshidrosiform eczema, age-caused wrinkles, sun damage itching, psoriasis vulgaris, flaking eczema, psoriasis pustulosa, psoriasis arthropatica, psoriatic erythroderma, *rosacea*, photodermatosis, radiodermatitis acuta and chronica (UV and ionizing radiation therapy), chronic actinic dermatitis, photouticaria (uticaria solaris), polymorphic photodermatosis, prurigo (strophulus, uticaria papulosa), subacuta, chronica, acne vulgaris, juvenile and adult (acne with comedones, papulous, pustulous, nodose, i.e., nodular, nodulocystic acne), acne conglobata (special form: hidradenitis suppurativa), acne fulminans, acne tetrad, acne neonatorum, senile acne, mechanical acne forms (excoriated acne), acne cosmetica, folliculitis with superinfected acne (*Staphylococci*), occupation-related acne forms (for example chlorine acne), decubitis, ulcus cruris, deficient ipoactive skin, localized scratch dermatitis rinophyma, ichthyosis, *xerosis*, and perioral dermatits.

* * * * *